(12) United States Patent
Fujii et al.

(10) Patent No.: US 7,597,443 B2
(45) Date of Patent: Oct. 6, 2009

(54) WIDE VIEWING ANGLE OCULAR FUNDUS BLOOD FLOW IMAGING DEVICE

(75) Inventors: Hitoshi Fujii, Fukuoka (JP); Naoki Konishi, Fukuoka (JP)

(73) Assignee: Kyushu Institute of Technology, Fukuoka (JP)

( * ) Notice: Subject to any disclaimer, the term of this patent is extended or adjusted under 35 U.S.C. 154(b) by 155 days.

(21) Appl. No.: 11/666,606

(22) PCT Filed: Oct. 27, 2005

(86) PCT No.: PCT/JP2005/019754

§ 371 (c)(1),
(2), (4) Date: Apr. 30, 2007

(87) PCT Pub. No.: WO2006/046627

PCT Pub. Date: May 4, 2006

(65) Prior Publication Data

US 2007/0291226 A1      Dec. 20, 2007

(30) Foreign Application Priority Data

Oct. 28, 2004   (JP) ............................. 2004-313307

(51) Int. Cl.
*A61B 3/10*   (2006.01)
*A61B 3/14*   (2006.01)

(52) U.S. Cl. ...................................... 351/205; 351/210

(58) Field of Classification Search ................. 351/205, 351/210

See application file for complete search history.

(56) References Cited

U.S. PATENT DOCUMENTS

| 5,163,437 A | 11/1992 | Fujii et al. |
| 2002/0118338 A1 * | 8/2002 | Kohayakawa ............... 351/206 |

FOREIGN PATENT DOCUMENTS

| JP | 4-242628 A | 8/1992 |
| JP | 9-173297 A | 7/1997 |
| JP | 9-238904 A | 9/1997 |
| JP | 2000-41946 A | 2/2000 |
| JP | 2003-546 A | 1/2003 |
| JP | 2003-164431 A | 6/2003 |
| JP | 2003-180641 A | 7/2003 |

OTHER PUBLICATIONS

Hitoshi Fujii, "Laser Speckle o riyou shita Ketsuryuugazoukagijutsu", Keisoku-to-seigyo (Measurement and Control), Japan, Apr. 4, 2000, vol. 39th, No. 4, pp. 246-252.

* cited by examiner

*Primary Examiner*—Jordan M. Schwartz
*Assistant Examiner*—James C Jones
(74) *Attorney, Agent, or Firm*—Sughrue Mion, PLLC

(57) ABSTRACT

Provided is a wide viewing angle ocular fundus blood flow imaging device in which the measurement field of view is enlarged and which includes a projection system that turns a laser beam into a rectangular spot on the ocular fundus, an observation system that images the rectangular spot on an image sensor placed on the corresponding image plane, an observation optical system for carrying out positioning of the laser spot, and a mechanism for monitoring the movement of an ocular fundus blood vessel image.

24 Claims, 8 Drawing Sheets

SIDE VIEW

VERTICAL VIEW

Figure 1:
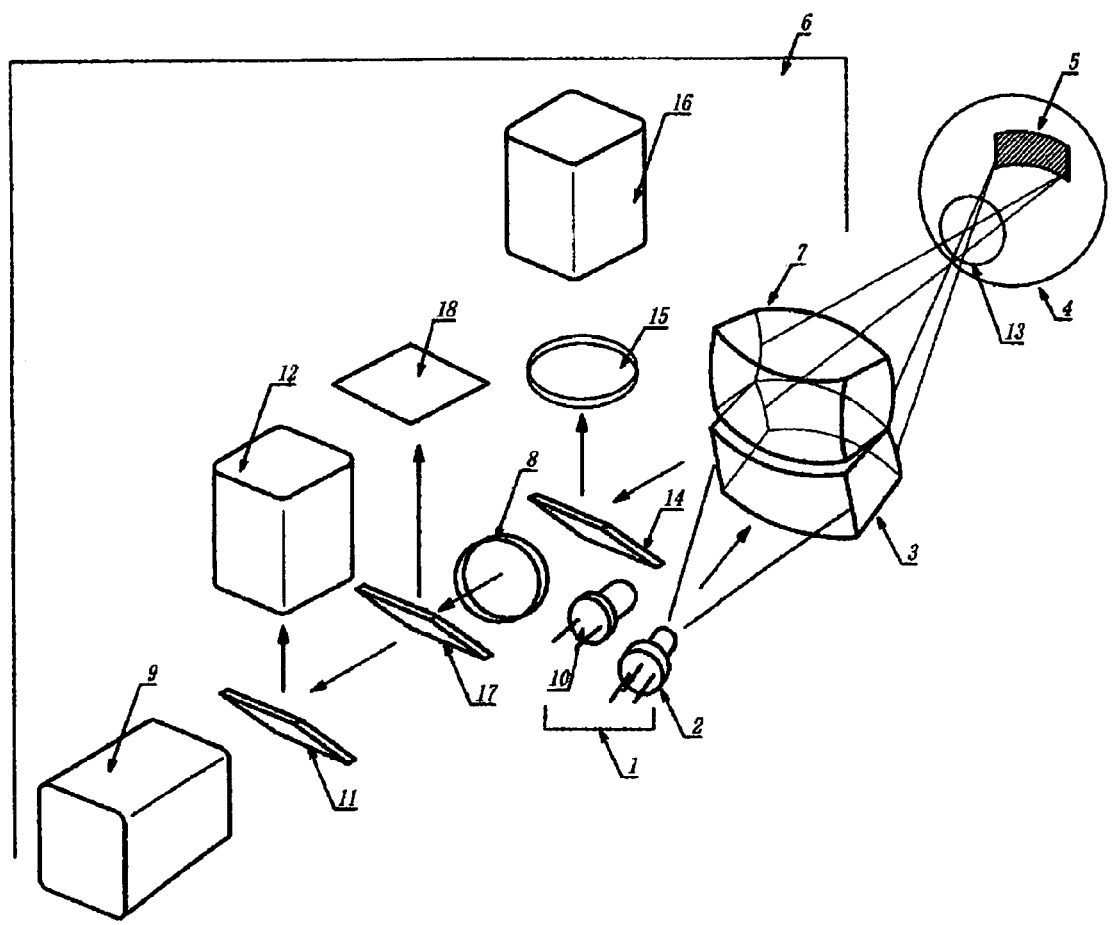

ANTERIOR EYE
OBSERVATION IMAGE (a)

CONVENTIONAL
INTERNAL FIXATION
TARGET (b)

NOVEL INTERNAL
FIXATION TARGET (● is LIT)

(a)

(b)

COMBINED

VARIATION OVER TIME OF AVERAGE BLOOD FLOW (a)

(b)

ANTERIOR EYE OBSERVATION IMAGE (a)

(b)

ANTERIOR EYE OBSERVATION IMAGE

BEFORE MOVEMENT

AFTER MOVEMENT

WIDE VIEWING ANGLE OCULAR FUNDUS BLOOD FLOW IMAGING DEVICE

TECHNICAL FIELD

The present invention relates to an ocular fundus blood flow imaging device for measuring a blood flow state of the ocular fundus of a subject's eye. More particularly, the present invention relates to a wide viewing angle ocular fundus blood flow imaging device that is an improvement over a conventional device and is clinically superior.

BACKGROUND ART

When body tissue such as the ocular fundus is irradiated with a laser, the laser is scattered by particles forming the body tissue, and an intensity distribution of reflected scattered light forms a dynamic laser speckle (random spot pattern) due to moving scattering particles such as blood cells. It is known that by detecting this pattern with an image sensor at an imaging plane, quantifying the change over time of the pattern for each pixel, and displaying it as a map, the blood flow distribution of blood capillaries in the vicinity of the body surface can be imaged.

There is a conventionally known blood flow rate measurement device employing such a phenomenon, in which blood cells of body tissue such as the ocular fundus of a subject's eye are irradiated with a laser, an image formed from light reflected from the blood cells is guided onto an image sensor such as a solid-state image pickup device (CCD camera), this image is captured and stored many times successively at predetermined time intervals, from the large number of stored images a predetermined number of images are selected, a value is calculated by integrating the change over time in the output from each pixel of each image, and the speed of blood cells (blood flow rate) is calculated from this value. In this type of blood flow rate measurement device, since the change in the output from each pixel corresponds to the speed of movement of blood cells, a blood flow rate distribution in the body tissue is displayed on a monitor screen as a two-dimensional image based on the value for the change in output from each pixel thus calculated, or the reciprocal thereof. This type of device is equipped with many calculation functions for use in clinical applications, and various improvements and modifications have been carried out for clinical applications.

(Patent Publication 1) JP-A-4-242628 (JP-A denotes a Japanese unexamined patent application publication)

(Patent Publication 2) JP-A-2003-164431

(Patent Publication 3) JP-A-2003-180641

(Non-Patent Publication 1) Keisoku-to-seigyo (Measurement and Control), Vol. 39, No. 4, pp. 246-252 (2000)

However, in the conventional device, since the laser spot on the ocular fundus is only on the order of a 3 mm square, the measurement region is limited, and in order to obtain data for blood flow over a wide area it is necessary to carry out measurement many times while changing the measurement position and combine these maps to give a large blood flow map, thus making the operation very complicated. Furthermore, for an actual patient, it is difficult to stare at one point because of impaired vision; during measurement the line of sight often moves (fixation movement), and when the measurement position deviates due to fixation movement, errors in reading a blood flow value easily occur, which is a problem.

With regard to the problem with fixation movement, the present inventors have already developed and proposed a calculation function for tracking fixation movement when fixation movement occurs during measurement by analyzing and correcting for the amount of movement, and accurately superimposing to give an average blood flow map (ref. Patent Publication 2). In this proposal, a provisional blood flow map is calculated for each screen obtained from an image sensor, and deviation of said map from an initial map is determined by calculating a spatial correlation. However, since a granular structure due to laser interference remains in the provisional blood flow map, when calculating relative positions between maps, a statistical error corresponding to the granular size occurs. That is, as long as an image captured by irradiating the ocular fundus with a laser is used, there is a limit to the performance in tracking fixation movement.

DISCLOSURE OF INVENTION

Problems to be Solved by the Invention

Imaging of ocular fundus blood flow found its main application field from the beginning in the measurement of change in blood flow in the narrow area of the optic papilla. However, there is a wide demand for macroscopic observation of blood circulation over the entire ocular fundus, such as the macular region (center of the visual field), and it is an object of the present invention to enlarge the viewing angle in order to meet the above-mentioned demand, that is, to provide a wide viewing angle ocular fundus blood flow imaging device. It is another object of the present invention to improve the conventional device in various aspects and to provide an ocular fundus blood flow imaging device that is clinically excellent and easy to use.

Means for Solving the Problems

The invention related to Claim 1 in order to attain the object of the present invention is a wide viewing angle ocular fundus blood flow imaging device comprising irradiating the ocular fundus with an expanded laser beam, imaging light reflected from the ocular fundus on a 2-dimensional image sensor as a laser speckle, and measuring for each pixel a change over time of the laser speckle generated on the image plane to thus display an image as a blood flow map, wherein the device comprises a projection system that turns a laser beam into a rectangular spot on the ocular fundus, and an, observation system that images the rectangular spot on an image sensor placed on the corresponding image plane.

The invention related to Claim 2 is the wide viewing angle ocular fundus blood flow imaging device according to Claim 1, wherein the projection system employs one or two beams as the laser beam.

The invention related to Claim 3 is the wide viewing angle ocular fundus blood flow imaging device according to Claim 1 or 2, wherein the major axis of an elliptical spot when the laser beam emerges is aligned with the major axis of the rectangular spot passing through the pupil. Aligning the major axis of the rectangular spot with the major axis of the elliptical spot when the laser emerges enables a uniform light intensity distribution to be achieved. If this alignment is not carried out, the light intensity distribution tends to decrease in a peripheral area in the major axis direction.

The invention related to Claim 4 is the wide viewing angle ocular fundus blood flow imaging device according to any one of Claims 1 to 3, wherein in the projection system the laser beam has a rectangular spot shape and passes through a lower part and/or an upper part of the pupil. When one laser beam is used, the beam passes through either the lower part or the upper part of the pupil, and when two laser beams are used, one thereof passes through the lower part and the other passes through the upper part.

The invention related to Claim 5 is a specific mode for carrying out the present invention related to Claim 4, and is the wide viewing angle ocular fundus blood flow imaging device according to Claim 4, wherein in the projection system a cylindrical lens is placed in the laser irradiation optical path, and at a position in front of a subject's eye the horizontal spread of the laser beam is minimized and the vertical spread is subsequently minimized. In this case, the rectangular spot is a spot that is long in the horizontal direction.

Furthermore, the invention related to Claim 6 is the wide viewing angle ocular fundus blood flow imaging device according to any one of Claims 1 to 3, wherein in the projection system the laser beam has a rectangular spot shape and passes through a left-hand part and/or a right-hand part of the pupil. When one laser beam is used, the beam passes through either the left-hand part or the right-hand part of the pupil, and when two laser beams are used, one thereof passes through the left-hand part of the pupil and the other passes through the right-hand part.

The invention related to Claim 7 is a specific mode for carrying out the invention related to Claim 6, and is the wide viewing angle ocular fundus blood flow imaging device according to Claim 6, wherein in the projection system a cylindrical lens is placed in the laser irradiation optical path, and at a position in front of a subject's eye the vertical spread of the laser beam is minimized and the horizontal spread is subsequently minimized. In this case, the rectangular spot is a spot that is long in the vertical direction.

The invention related to Claim 8 is the wide viewing angle ocular fundus blood flow imaging device according to any one of Claims 1 to 7, wherein the device has incorporated thereinto an optical system for observing the position of a laser beam spot passing through the pupil, and comprises a mechanism for carrying out appropriate control of positioning of the blood flow measurement optical system based on image information obtained.

The invention related to Claim 9 is the wide viewing angle ocular fundus blood flow imaging device according to any one of Claims 1 to 8, wherein the device has incorporated thereinto a mechanism for adjusting gaps between a plurality of spots.

The invention related to Claim 10 is the wide viewing angle ocular fundus blood flow imaging device according to any one of Claims 1 to 9, wherein the device has incorporated thereinto a mechanism for monitoring the movement of an ocular fundus blood vessel image by means of a different observation system from that for imaging such that, when the ocular fundus is irradiated with a laser so as to image the ocular fundus blood flow, the same position in the ocular fundus is simultaneously illuminated with incoherent light.

The invention related to Claim 11 is the wide viewing angle ocular fundus blood flow imaging device according to any one of Claims 1 to 10, wherein the monitoring mechanism comprises a method in which ocular fundus image data obtained by laser and ocular fundus image data obtained by incoherent light are collated.

The invention related to Claim 12 is the wide viewing angle ocular fundus blood flow imaging device according to any one of Claims 1 to 11, wherein as an internal fixation target for a subject whose eye is to be tested a fixation target is lit in a cross shape utilizing a light-emitting diode (LED) matrix.

The invention related to Claim 13 is the wide viewing angle ocular fundus blood flow imaging device according to any one of Claims 1 to 12, wherein the device has incorporated thereinto a mechanism for automatically driving the entire observation system in vertical and lateral directions in response to vertical and lateral movement of the fixation target.

The invention related to Claim 14 is the wide viewing angle ocular fundus blood flow imaging device according to any one of Claims 1 to 13, wherein the device has incorporated thereinto a mechanism for forming one large map by calculating relative positions between a plurality of maps and combining the maps based on light-emitting diode (LED) matrix coordinates of the fixation target.

The invention related to Claim 15 is the wide viewing angle ocular fundus blood flow imaging device according to any one of Claims 1 to 14, wherein the device has incorporated thereinto a mechanism that, when storing a measured blood flow map in a file, stores data for the positional coordinates of the fixation target when the eye is tested in a header part of the file or another database, reads these data when testing the eye the next time, and automatically sets the position of the fixation target.

The invention related to Claim 16 is the wide viewing angle ocular fundus blood flow imaging device according to any one of Claims 1 to 15, wherein the device has incorporated thereinto a function for calculating a difference between data obtained on different eye testing occasions and displaying an image of increases and decreases in blood flow.

The invention related to Claim 17 is the wide viewing angle ocular fundus blood flow imaging device according to any one of Claims 1 to 16, wherein the device has incorporated thereinto a function for calculating an autocorrelation function with respect to a waveform of average blood flow in the ocular fundus and separating a series of map data arranged in chronological order using an average period by taking the time from the center of one peak to the next as one period, and a calculation function for determining the time relationship for optimum overlap by superimposing average blood flow waveforms of the group of separated maps.

The invention related to Claim 18 is the wide viewing angle ocular fundus blood flow imaging device according to any one of Claims 1 to 17, wherein the device has incorporated thereinto a function for retrieving as a signal an exposure timing of the above-mentioned 2-dimensional image sensor, irradiating the ocular fundus with laser only for the time for which each element of this sensor is exposed, and reducing the laser output for the time other than the above, thus reducing the amount of laser bombardment that the ocular fundus receives.

The invention related to Claim 19 is the wide viewing angle ocular fundus blood flow imaging device according to any one of Claims 1 to 18, wherein an emergent laser optical system is inserted between the subject's eye and an objective lens for observation of the ocular fundus so as to prevent intrusion of a specular reflection component of the laser spot into the blood flow image.

The invention related to Claim 20 is the wide viewing angle ocular fundus blood flow imaging device according to any one of Claims 1 to 19, wherein by changing the fixation target position during measurement of the blood flow, the influence of seams between a plurality of laser spots is prevented from appearing on the blood flow map.

BRIEF DESCRIPTION OF DRAWINGS (FIG. 1) A schematic diagram showing the configuration of an optical system of the wide viewing angle ocular fundus blood flow imaging device of the present invention.

(FIG. 2) A diagram for explaining the spread of a laser beam at a position in front of the pupil surface of a subject's eye in the present invention.

(FIG. 3) A diagram for explaining the position of a laser spot that passes through the pupil when starting measurement in the present invention.

(FIG. 4) A diagram for explaining a state in which a fixation target is lit in the present invention.

(FIG. 5) A diagram showing a mechanism for automatically driving the entire observation system vertically in response to vertical movement of the fixation target in the present invention.

(FIG. 6) A diagram for explaining a method of combining a plurality of maps based on LED coordinates of the fixation target in the present invention.

Figure 7:
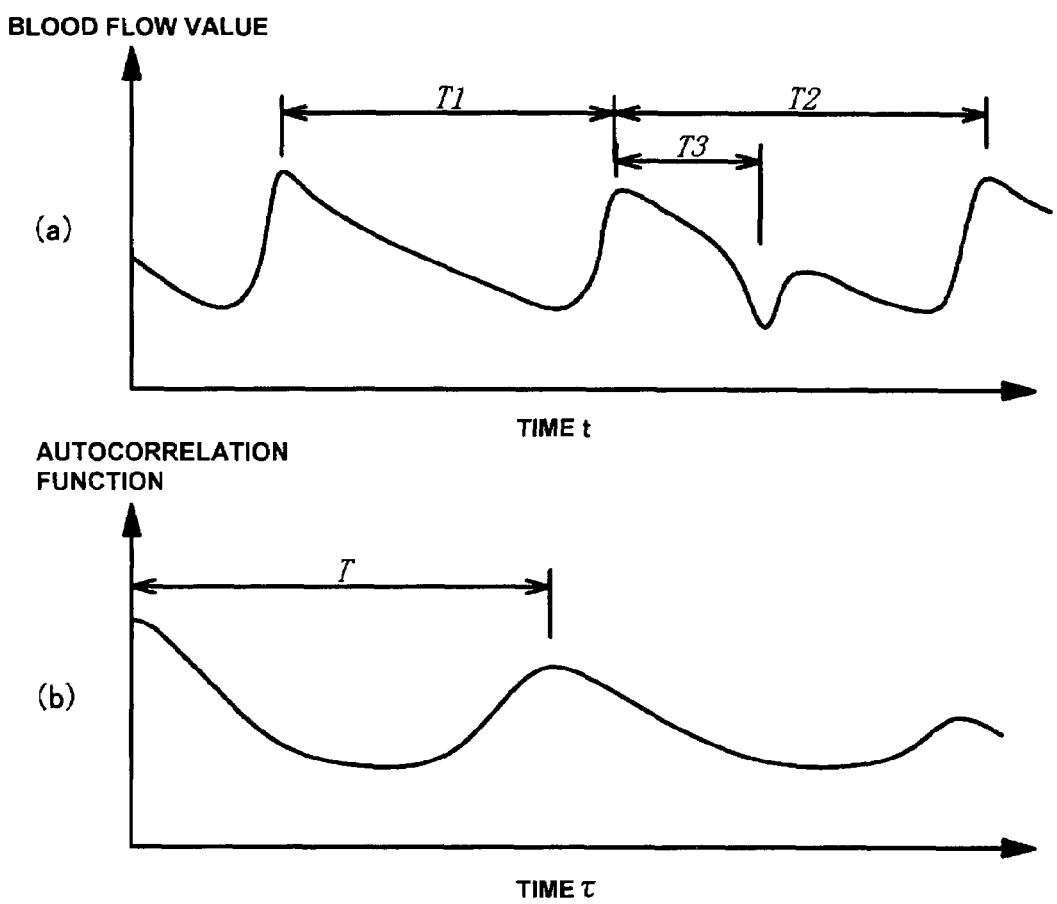

(FIG. 7) A diagram for explaining map synthesis in the present invention.

(FIG. 8) A diagram for explaining variations in average blood flow over time in map synthesis in the present invention.

(FIG. 9) A diagram showing a signal denoting exposure timing of a 2-dimensional image sensor and the relationship between exposure time of each element of the sensor and laser irradiation time in the present invention.

(FIG. 10) A diagram for explaining the positional relationship between the laser spot on the ocular fundus and the spot passing through the pupil surface when the ocular fundus is illuminated by passing two laser beams through upper and lower edges of the pupil.

(FIG. 11) A diagram for explaining the positional relationship between the laser spot on the ocular fundus and the spot passing through the pupil surface when the ocular fundus is illuminated by passing two laser beams through left-hand and right-hand edges of the pupil.

(FIG. 12) A diagram showing a state in which, when the ocular fundus is illuminated by passing two laser beams through left-hand and right-hand edges of the pupil, another lens used exclusively for laser irradiation is provided between the eyeball and the objective lens.

(FIG. 13) A diagram showing that, when there is a gap between laser spots, data for the spot boundary can be acquired by moving the ocular fundus by changing the position of the fixation target that is lit up during measurement.

BEST MODE FOR CARRYING OUT THE INVENTION

The present invention comprises a projection system in which a laser beam is turned into a rectangular spot on the ocular fundus and an observation system in which this rectangular spot is imaged on an image sensor placed on the corresponding image plane, and the rectangular spot referred to in the present invention (the inventions of all Claims) includes a horizontally long or vertically long elliptical shape and a semicircular spot. One, or two or more beams may be used as the laser beam, but one or two beams are preferable in terms of simplicity.

In the present invention, since the spot shape is rectangular when it passes through the pupil, it is possible to expand the spot along the edge of the pupil. It is therefore possible to irradiate as wide an area of the ocular fundus as possible while making the beam pass through just inside the pupil. Specifically, the laser beam preferably has a rectangular spot shape and is passed through a lower part and/or an upper part of the pupil when viewed from the center of the pupil or, by rotating this spot through 90 degrees, a left-hand part and/or a right-hand part of the pupil. It is more preferable for the laser beam to pass through a lower edge and/or an upper edge of the pupil or a left-hand edge and/or a right-hand edge of the pupil. When two beams are used, it is preferable for them to pass through diagonal positions of the pupil such as the upper part and the lower part of the pupil or the left-hand part and the right-hand part of the pupil. Furthermore, in the projection system of the present invention it is preferable to insert a cylindrical lens in the laser irradiation optical path. It is possible to intentionally add astigmatism by inserting the cylindrical lens, and diffuse the light intensity when the spot is a minimum.

Among the present inventions, an embodiment in which one laser beam is used and this is passed through a lower part of the pupil is explained by reference to the drawings. FIG. 1 is a schematic diagram showing the configuration of an optical system of the wide viewing angle ocular fundus blood flow imaging device of the present invention. 1 denotes a projection system, laser light coming out of a small-size laser source 2, such as a semiconductor laser, of the projection system 1 is expanded by passing it through, for example, a cylindrical lens 3, and irradiates the ocular fundus of a tested eye 4 as a rectangular (horizontally long) spot 5. 6 denotes an observation system, and light reflected from the laser spot 5 is imaged via imaging lenses 7, 8 as a laser speckle on an image sensor, such as for example a CCD (solid-state image pickup device) camera 9, placed on the corresponding image plane. Change over time of the laser speckle formed on the image plane is measured for each pixel, thus displaying an image as a blood flow map.

The projection system 1 has incorporated thereinto an incoherent light source such as a green LED 10, and it illuminates the same place as the ocular fundus location that is irradiated with the semiconductor laser 2. This green light spot passes through the imaging lenses 7, 8, is then separated into a different light path by means of a wavelength-selective mirror such as a dichroic mirror 11, and imaged on another image sensor 12 as an ocular fundus image. Data from this sensor 12 are sent to a signal analysis system at the same time as data from the CCD camera 9 and used for analysis of information on the amount of movement of the ocular fundus.

Furthermore, there is also incorporated an optical system that turns around the light reflected from a pupil surface 13 by means of a different dichroic mirror 14 and observes an image of the pupil surface by means of a lens 15 and a different image sensor 16. It is possible to confirm, based on this image, whether or not the laser spot passes precisely through a predetermined position of the pupil. Moreover, another dichroic mirror 17 is inserted partway along the observation system light path, and an internal fixation target 18 given by a light-emitting diode matrix is installed so as to be on the image plane of the ocular fundus. A subject whose eye is to be tested stares at the light spot position of the matrix so as to fix the line of sight.

When testing an eye, it is desirable that as extensive a blood flow map as possible is obtained by one measurement, and from the viewpoint of safety and low irritation toward the eye, the light intensity passing through the ocular fundus and the pupil should be reduced as much as possible. Overlapping the projection system and the observation system by means of a half mirror increases the specular reflection component from an objective lens and the cornea. Since the half mirror causes light loss, the laser light intensity with which the ocular fundus is irradiated has to be doubled. If the two are separated so that the laser irradiation optical path does not block the observation light path, there is a limit to the vertical expansion of the observation field. In this embodiment of the present invention, the laser expands horizontally and an optical system is arranged so as to observe this horizontally expanded spot 5, thereby enabling the observation field of view to be enlarged.

Figure 2:
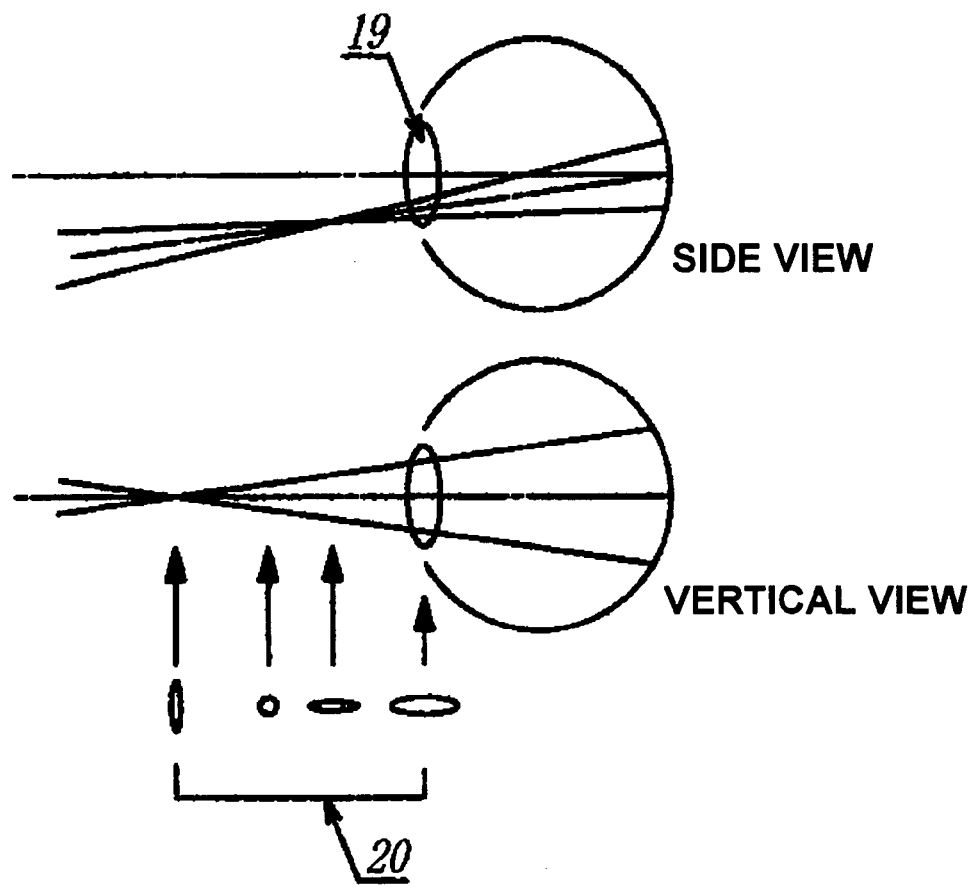

When the laser spot passes through the pupil, if the laser spot is narrowed down too much, there is a possibility of injuring the surface of the iris. In order to solve this problem, for example, the cylindrical lens 3 is placed in the laser irradiation optical path of the projection system 1, and as shown in FIG. 2 at a position in front of the pupil surface 19 of the subject's eye the horizontal spread of the laser beam is minimized and the vertical spread is then minimized. That is, this forms an optical system that artificially imparts a high degree of astigmatism. Using the cylindrical lens 3 prevents the spot shape 20 from becoming a point at any position in front of the pupil surface and enables the area of the spot passing through the pupil to become larger than would be the case if the light was simply focused by a spherical lens. In this process, as shown in FIG. 2, it is preferable for the shape of the spot when the laser passes through the lower part of the pupil to be long in the horizontal direction. By so doing, even if the spot falls on the iris, any possibility of damaging the iris can be excluded. If the spot is vertically expanded at the lower part of the pupil, the lower part is cut off by the pupil, and the upper part is specularly reflected, thus causing fogging that becomes ghosting in the detection system. Furthermore, since a laser spot shape is generally elliptical, in order to make the light intensity distribution within the rectangular spot as uniform as possible, it is preferable for the major axis of the ellipse to be aligned horizontally.

Figure 3:
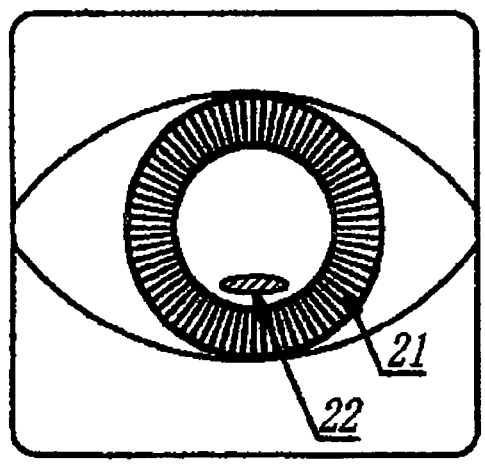

Positioning of the laser spot passing through the pupil is extremely important. If it is inadequate, the laser beam cannot reach the ocular fundus and the periphery of a blood flow map is incomplete. Therefore, in the present invention, as shown in FIG. 3, an optical system is incorporated for observing the position of the laser spot 22 passing through the pupil 21 when starting measurement. In order to do this, for example, in FIG. 1 it is made possible for an image of the pupil area to be observed by the image sensor 16, and by incorporating a mechanism that, when the positioning is inadequate, issues a warning or automatically moves the optical system to the optimum position, the problem can be solved.

Figure 4:
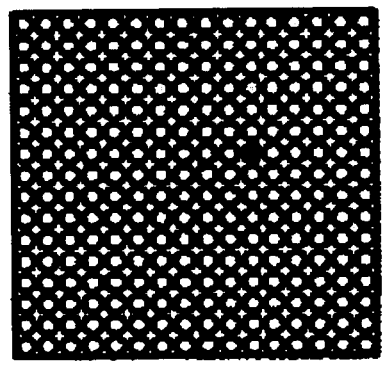
Figure 4:
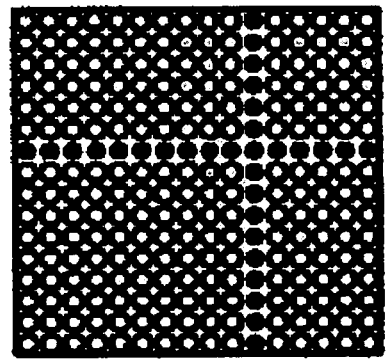
Figure 5:
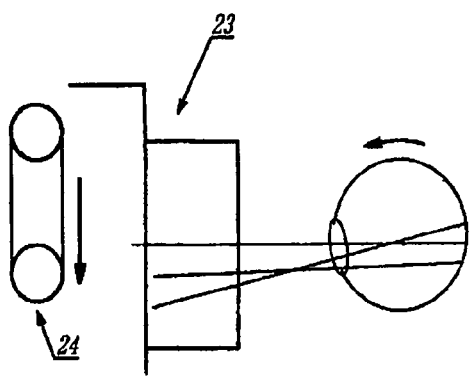
Figure 5:
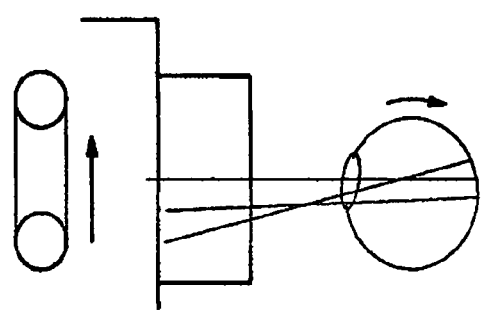

In the present invention, as shown in FIG. 4, for example, an LED matrix is used as an internal fixation target, and it is preferable for the fixation target to be lit in the shape of a cross. Conventionally, as shown in FIG. 4 (*a*), the fixation target is displayed by one LED, but there is the problem that it is not visible to a subject having poor central vision. However, as shown in FIG. 4 (*b*), if it is lit in the shape of a cross, even it is impossible to see the central part, fixation becomes relatively stable. Furthermore, as shown in FIGS. 5 (*a*) and (*b*), positioning of the observation system is carried out by incorporating a mechanism 24 that automatically drives the entire observation system 23 vertically in response to vertical movement of the fixation target while keeping the line of sight horizontal; after the blood flow is measured the fixation point is moved upward, thus solving the problem that, when a part above the center of the ocular fundus is measured, the eyeball rotates, the position of the pupil moves upward, and the lower part of the laser beam is cut off.

Furthermore, in the present invention, as shown in FIG. 1, it is preferable to incorporate the mechanism for monitoring movement of an ocular fundus blood vessel image by means of a different observation system from that for measurement such that, when the ocular fundus is irradiated with a laser so as to measure the blood flow, the ocular fundus is simultaneously illuminated with incoherent light 10 such as a green LED. Providing such a monitoring mechanism enables information on the movement of the ocular fundus to be analyzed and an average blood flow map to be synthesized by superimposing while correcting deviations on the blood flow map side even if the line of sight of the subject is unstable and the ocular fundus moves during the measurement. Conventionally, information on the amount of movement is calculated using only a blood flow map, and since a random granular pattern is superimposed on the map due to the laser interference effect, this granular structure causes errors, thus making it impossible to track the movement of the ocular fundus with high precision. As in the present invention, if the ocular fundus is irradiation with an LED, which exhibits no interference effect, the granular structure does not appear, and the tracking performance improves.

In this process, it is preferable for the monitoring mechanism to employ a method in which the ocular fundus image data obtained by laser and the ocular fundus image data obtained by incoherent light are collated, that is, a method in which superimposing is carried out while correcting deviations on the blood flow map side by a post-treatment, since analysis and correction of information relating to movement then become easy.

Figure 6:
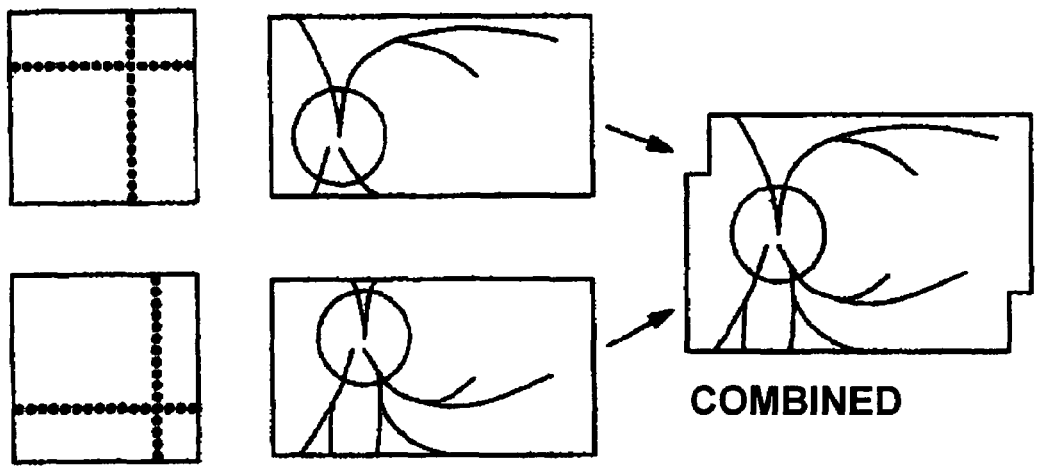

Moreover, in the present invention, as schematically shown in FIG. 6, it is also preferable to incorporate a mechanism for forming one large map by calculating relative positions between a plurality of maps and combining the maps based on LED coordinates of the fixation target. Conventionally, maps are combined by manually specifying common characteristics of two maps (step 1) and determining by calculation the position in which these characteristics best overlap each other (step 2). Use of the LED coordinates enables step 1 to be omitted, and fully automatic joining of the maps to be rapidly carried out.

In the present invention, it is preferable to incorporate a mechanism for automatically setting the fixation position if data for the coordinates of the fixation target when measurement is carried out are stored in a header part of the blood flow map file or another database, and these data are read out using a patient chart number, etc. the next time the measurement is carried out. When a therapeutic effect is confirmed, it is necessary to measure changes in blood flow at the same position at fixed time intervals. In conventional devices, much effort has been expended in order to guide the fixation to a position in which the same map as the previous blood flow map could be obtained, while looking at the previous map. There was no means for precisely guiding the fixation to the previously measured position. Using the lit-up position of the LED matrix enables 100% reproduction of the fixation to be obtained.

Moreover, in the present invention, it is preferable to incorporate a function for displaying increases and decreases in blood flow as an image by calculating the difference from previously measured data and displaying it. In order to confirm a therapeutic effect, for example, confirmation of whether or not there is a tendency for the blood flow to increase as a result of eye drops relative to the previous occasion is desired. If the reproducibility of fixation improves, the distribution of increases and decreases can be observed at a glance by calculating the difference from the previous occasion.

Figure 8:
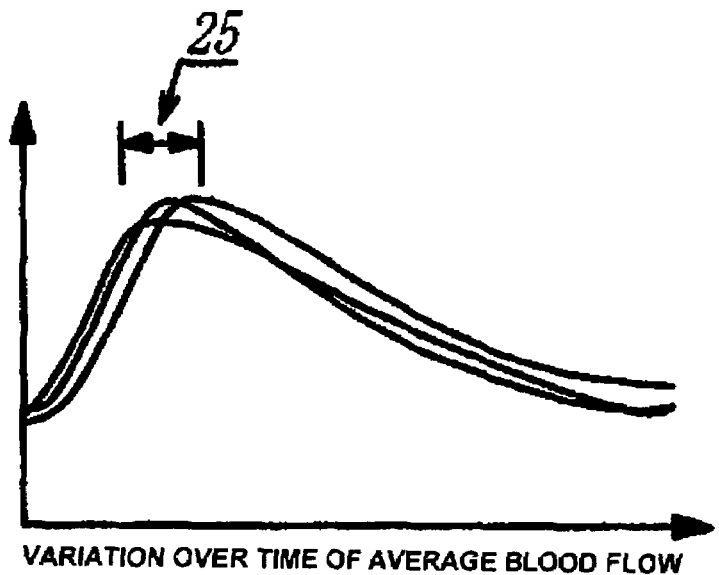

The operation of averaging blood flow maps measured for several seconds with respect to 1 heart beat is called 'map synthesis'. In a procedure for dividing these series of blood flow map data into the phases of a heart beat, it is unexpectedly difficult to analyze one period. In particular, when a map having a low blood flow part way through due to blinking, etc. is incorporated, this is recognized as a minimum value and the calculated period becomes short. For example, as in FIG. 7 (a), although the blood flow value varies periodically over time, if a low value caused by blinking, etc. is inserted during T1 or T2, which are proper periods, T3 might be erroneously recognized as a period instead of T2. In such a case, since the blood flow maps cannot be superimposed correctly during synthesis, an analytical error occurs. In order to solve this problem, a function is incorporated for calculating an autocorrelation function with respect to the waveform of the average blood flow (FIG. 7 (b)) and separating a series of map data using an average period T by taking the time from the center of one peak to the next as one period. When there is a fluctuation in the period of the heart beat due to arrhythmia, etc., if an average period is obtained by the above-mentioned method and a series of maps over time are superimposed by separating at equal intervals based on the above period, as shown in FIG. 8, an error 25 occurs due to variations in the phase. In order to solve this problem, it is preferable to incorporate a function for determining a correlation between the waveforms of each heart beat in sequence and determining the time relationship for optimum waveform overlap before superimposing them.

Figure 9:
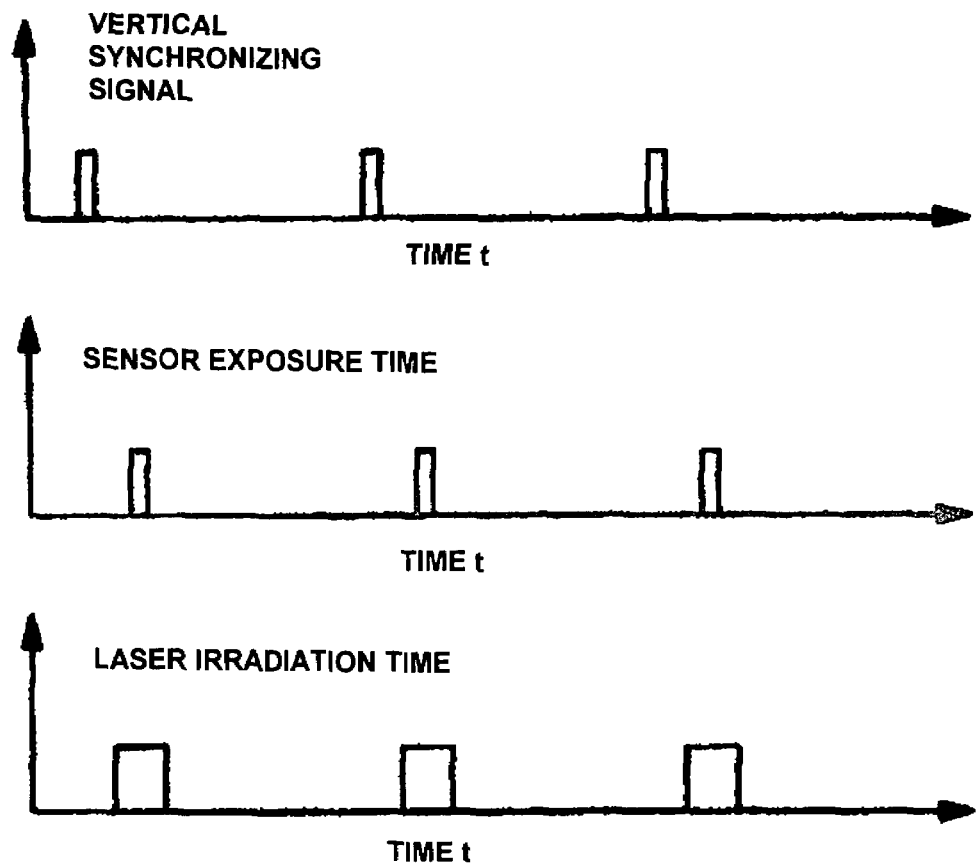

Furthermore, in the present invention, in order to reduce the laser bombardment that the ocular fundus receives during eye testing and enhance the safety, it is preferable to incorporate a function for retrieving as a signal the exposure timing of the above-mentioned 2-dimensional image sensor by a method shown in FIG. 9, irradiating the ocular fundus with laser only for the time for which each element of this sensor is exposed, and reducing the laser output for the time other than the above.

When one laser beam is used and passed through an upper part of the pupil, or when the beam is passed through a left-hand part or a right-hand part of the pupil, this can be carried out by basically the same method as in the above-mentioned case.

Figure 10:
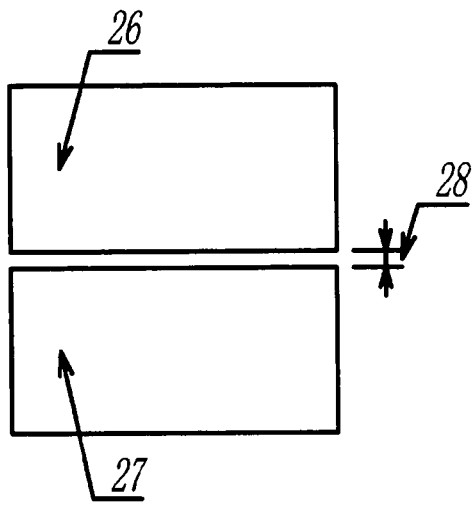
Figure 10:
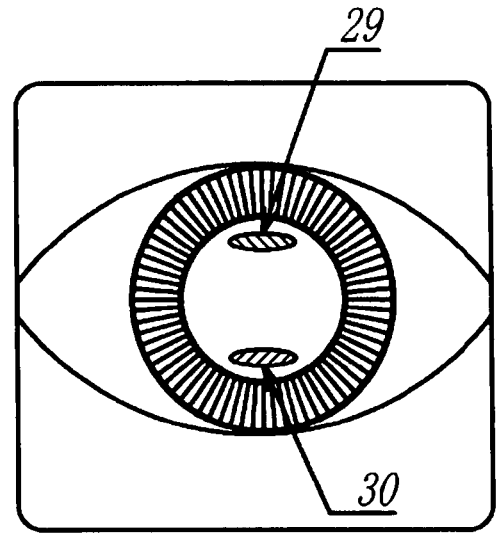

An embodiment of the present invention in which two laser beams are used is now explained by reference to the drawings. The basic optical system is the same as in the case of FIG. 1. As in FIG. 10 (b), when two laser beams pass through an upper part 29 and a lower part 30 of the pupil, as shown in FIG. 10 (a), in the ocular fundus, the beam from the lower part of the pupil forms a rectangular (horizontally long) spot 26 in an area above the middle of the ocular fundus and the beam from the upper part forms a rectangular (horizontally long) spot 27 in an area below the middle of the ocular fundus. A mechanism for adjusting a distance (gap) 28 between the two so that these spots are substantially joined to each other is provided. In addition, these spots are captured as a speckle image using one (several when the resolution is increased) CCD camera, thus making it possible to image a wide coverage blood flow map with one measurement (or image by joining a plurality of blood flow maps).

Figure 11:
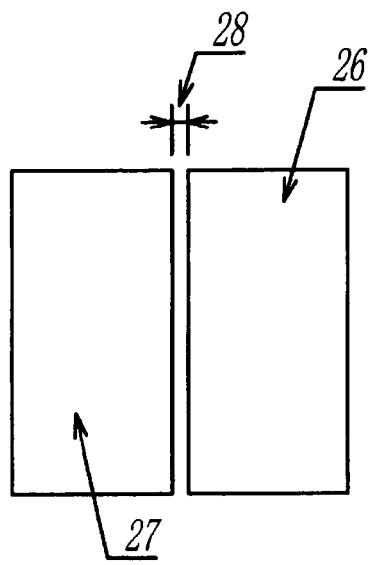
Figure 11:
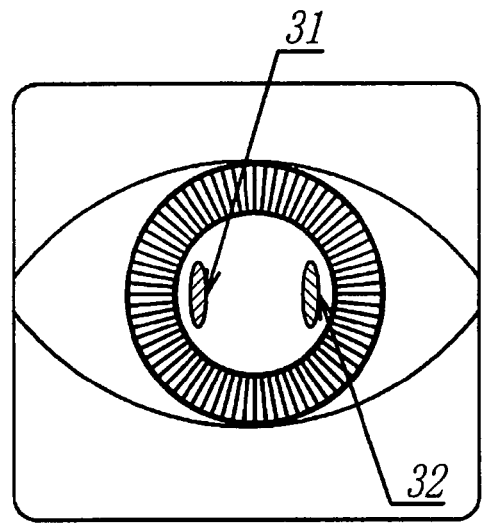

This also applies to a case in which two laser beams are used and passed through left-hand and right-hand edges of the pupil so as to arrange two vertically long spots side by side on the ocular fundus. As shown in FIG. 11 (b), by passing a plurality of laser beams through a left-hand edge 31 and a right-hand edge 32 of the pupil, spots can be arranged side by side on the ocular fundus as shown in FIG. 11 (a). This also enables a wide coverage blood flow map to be imaged by one measurement.

By separately providing a camera for observing a laser spot passing through the pupil surface, it is possible to carry out alignment between the eyeball and the observation system. When one spot passes through the pupil, it is rather difficult to work out the distance between the eyeball and the observation system, but when there are two spots 29 and 30 or 31 and 32, etc., if the distance of the eyeball and the observation system is appropriate, the gap becomes a preset value. By utilizing this effect, it is possible to optimize the distance between the eyeball and the observation system, or construct an automatic positioning mechanism.

Figure 12:
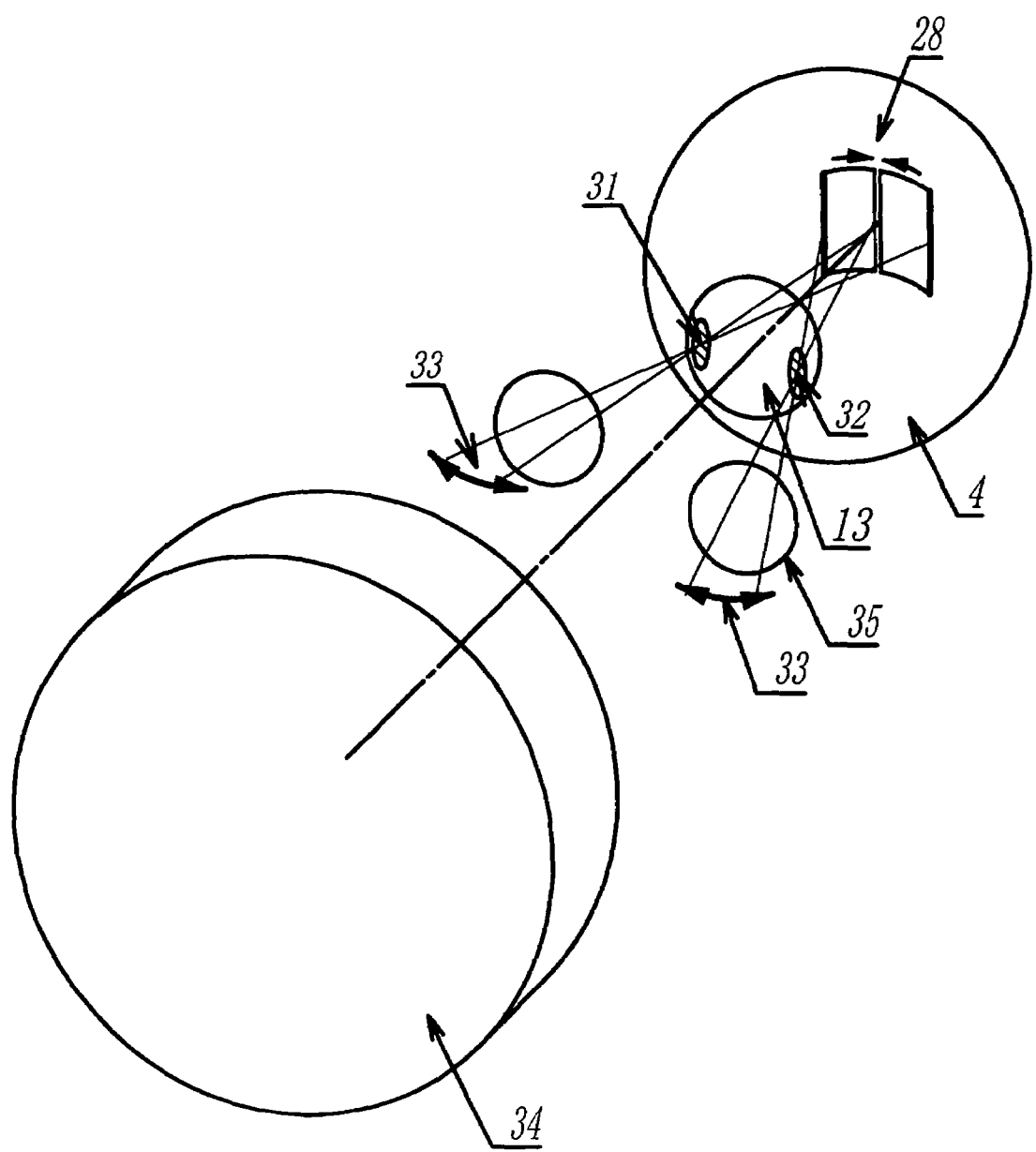
Figure 13:
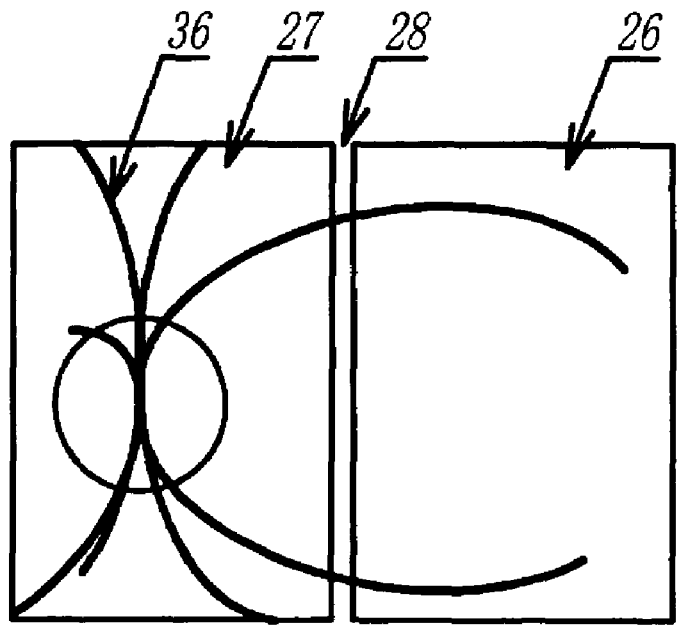
Figure 13:
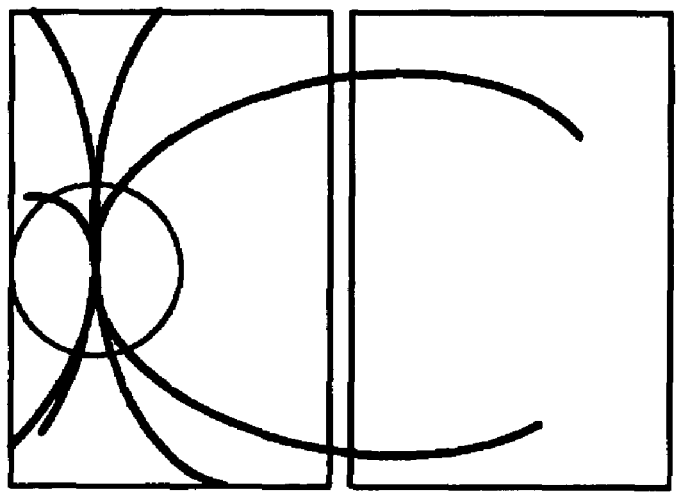

Since the length of the eyeball (depth of the eyeball) varies among individuals, two spots might be separated or might overlap. As a result, a place where data cannot be obtained occurs within a blood flow map in the form of a line. As a method for solving this, as shown in FIG. 12, providing a mechanism for adjusting the gap 28 between the spots by changing an angle 33 of the optical axis of two laser beams enables the laser spots to be joined to each other and one large blood flow map to be imaged. Alternatively, even if two laser spots are not completely joined and as shown in FIG. 13 the gap 28 occurs between the spots, by slightly moving the fixation target point during measurement, the measurement position for the ocular fundus (line of ocular fundus blood vessel) 36 is displaced to thus eliminate the site where data cannot be obtained.

Furthermore, in order to obtain an ocular fundus blood flow map with as wide an area as possible with one measurement, it is necessary to enlarge the spot itself projected on the ocular fundus and increase the angle of view of the observation system. However, in a method in which the ocular fundus is irradiated with laser through an objective lens for observing the ocular fundus, since the laser beam passes through the vicinity of the optical axis of the observation system, a specular reflection component is generated at the surface of an intermediate field lens, etc. and a strong bright point appears on the image of the ocular fundus. This bright point results in a region in the blood flow map where data cannot be obtained. This problem can be solved by providing, as shown in FIG. 12, another lens 35 exclusively used for laser irradiation between the tested eye 4 and the objective lens 34 and allowing the laser beam to be incident on the lens 35 by reflecting it by means of a mirror, etc. from the side. In this case, it is preferable to install the lens exclusively used for laser irradiation and the reflecting mirror without blocking the light path of the ocular fundus observation system and use a lens having a short focal length so that the laser beam forms a sufficiently large spot on the ocular fundus.

INDUSTRIAL APPLICABILITY

In accordance with the present invention, a wide viewing angle ocular fundus blood flow imaging device that is clinically excellent and easy to use is provided, and this is extremely useful for research into therapeutic methods and the development of drugs, etc. for many eye diseases such as age-related macular degeneration and glaucoma, for which the number of patients is expected to increase in future as the aging of society progresses.

In accordance with the invention of Claim 1, since the optical system is formed so that the laser irradiation expands horizontally or vertically and the spot thereof is observed, an ocular fundus blood flow imaging device giving a horizontally or vertically expanded measurement field of vision is provided. Furthermore, since the spot shape of the laser when it passes through the pupil is a rectangle, the light intensity per unit area decreases, the safety with respect to the eye is excellent, and there is little irritation. In the invention of Claim 2, one or two beams are used as the laser beam, and when two beams are used a wide coverage blood flow map can easily be obtained. In the invention of Claim 3, since the major axis of the rectangular spot is aligned with the major axis of the elliptical spot of the laser when it emerges, the light intensity distribution can be made uniform.

In accordance with the invention of Claims 4 to 7, since the major axis of the elliptical spot that naturally emerges from a semiconductor laser is either horizontal or vertical, the light intensity distribution within the rectangular spot projected onto the ocular fundus can be made substantially uniform. Furthermore, since the cylindrical lens is placed in the laser irradiation optical path, compared with a case in which light is condensed simply by means of a spherical lens, the area of the spot that passes through the pupil can be enlarged. In accordance with the invention of Claim 8, since it incorporates the optical system for observing the position of the laser spot that passes through the pupil when measurement is started, it is possible to precisely position the laser spot that passes through the pupil. In accordance with the invention of Claim 9, since it incorporates the mechanism for adjusting the gaps between a plurality of spots, it is possible to precisely synthesize a blood flow map.

In accordance with the invention of Claim 10, since it incorporates the mechanism in which, when blood flow is measured by irradiating the ocular fundus with laser, the ocular fundus is simultaneously illuminated with incoherent light such as a green LED and movement of the ocular fundus blood vessel image is monitored by means of the different observation system from that for measurement, even if the stability of the line of sight is poor and the ocular fundus moves during measurement, by superimposing maps while analyzing information on the movement of the ocular fundus and correcting for deviations on the blood flow map side an average blood flow map can be synthesized. In accordance with the invention of Claim 11, since the above-mentioned monitoring mechanism comprises the method in which the ocular fundus image data obtained by laser and the ocular fundus image data obtained by incoherent light are collated, it is easy to analyze and correct the information on the movement.

In accordance with the invention of Claim 12, since the fixation target is lit in a cross shape, in the case of a subject having poor central vision, there is an effect in making the fixation relatively stable even when the central area cannot be seen. In accordance with the invention of Claim 13, since it provides the function for moving the entire laser projection system and observation system in vertical and lateral directions in response to movement of the position of the fixation target, it is possible to easily position the observation system.

In accordance with the invention of Claim 14, since it incorporates the mechanism for forming one large map by calculating relative positions between a plurality of maps and combining the maps based on LED coordinates of the fixation target, it becomes possible to fully automatically combine the maps. In accordance with the invention of Claim 15, since it incorporates the mechanism that, when storing a measured blood flow map in a file, stores data for the fixation positional coordinates when the eye is tested in the header part of the blood flow map file or another database, reads these data at the time of the next measurement by means of, for example, a patient chart number, and thus automatically sets the fixation position, it is possible to precisely guide the fixation to the place that was measured on the previous occasion. In accordance with the invention of Claim 16, since it incorporates the function for calculating the difference from data obtained previously and displaying an image of increases and decreases in the blood flow, it is possible to easily confirm the therapeutic effect of, for example, eye drops.

In accordance with the invention of Claim 17, with regard to an operation of combining and averaging, with respect to 1 heart beat, blood flow maps measured for several seconds, it incorporates the function for calculating an autocorrelation function with respect to the average blood flow waveform within the ocular fundus region and separating a series of map data using the average period by taking the time from the center of one peak to the next as one period. In a case where the period of each heart beat fluctuates due to arrhythmia, etc., if combining and averaging is carried out for 1 heart beat as it is, overlapping is carried out while out of synchronization, and there is the problem that the change in blood flow cannot be precisely captured, but by incorporating a calculation function for determining the time relationship for optimum overlap by superimposing average blood flow waveforms of the group of separated maps in order to take this group of separated maps into synchronization with each other, the problem can be solved.

In the invention of Claim 18, since it incorporates the function for retrieving as a signal the exposure timing of the above-mentioned 2-dimensional image sensor, irradiating the ocular fundus with laser only for the time for which each element of this sensor is exposed, and reducing the laser output for the time other than the above, the amount of laser bombardment that the ocular fundus receives can be reduced, and the safety is excellent. In the invention of Claim 19, since the emergent laser optical system is inserted between the subject's eye and the objective lens for observation of the ocular fundus, it is possible to prevent intrusion of the specular reflection component of the laser spot into the blood flow image. In the invention of Claim 20, by changing the fixation target position during measurement of blood flow, the influence of seams between a plurality of laser spots is prevented from appearing on the blood flow map.

What is claimed is:

1. A wide viewing angle ocular fundus blood flow imaging device comprising:
    means for irradiating an ocular fundus with an expanded laser beam;
    means for imaging light reflected from the ocular fundus on a 2-dimensional image sensor as a laser speckle; and
    means for measuring, for each pixel of the laser speckle, a change over time of the laser speckle generated on an image plane, and for displaying a blood flow map based on the measured change,
    wherein the means for irradiating comprises a projection system that employs two laser beams and turns each of the two laser beams into respective rectangular spots on the ocular fundus, wherein each of the respective rectangular spots is disposed on a different region of the ocular fundus, and the means for imaging comprises an observation system that images the rectangular spots on the 2-dimensional image sensor placed on the corresponding image plane.

2. The wide viewing angle ocular fundus blood flow imaging device according to claim 1, wherein a major axis of an elliptical spot when the expanded laser beam emerges is aligned with a major axis of the rectangular spot passing through a pupil.

3. The wide viewing angle ocular fundus blood flow imaging device according to claim 1, wherein in the projection system the two laser beams have a rectangular spot shape and pass directly through a lower part and an upper part of the pupil, respectively.

4. The wide viewing angle ocular fundus blood flow imaging device according to claim 3, wherein the projection system comprises a cylindrical lens placed in a path of at least one of the two projected laser beams, and the projection system is configured to minimize, at a position in front of a subject's eye, a horizontal spread of the two laser beams, and further configured to minimize a vertical spread of the two laser beams after the minimization of the horizontal spread.

5. The wide viewing angle ocular fundus blood flow imaging device according to claim 1, wherein in the projection system the two laser beams have a rectangular spot shape and pass directly through a left-hand part and a right-hand part of a pupil, respectively.

6. The wide viewing angle ocular fundus blood flow imaging device according to claim 5, wherein in the projection system comprises a cylindrical lens placed in a path of at least one of the two projected laser beams, and the projection system is configured to minimize, at a position in front of a subject's eye, a vertical spread of the laser beams, and further configured to minimize a horizontal spread of the laser beams after the minimization of the vertical spread.

7. The wide viewing angle ocular fundus blood flow imaging device according to claim 1, further comprising:
   an optical system for observing a position of a laser beam spot passing through a pupil, and for obtaining image information based on the observed position;
   and means for carrying out appropriate control of positioning of the optical system based on the obtained image information.

8. The wide viewing angle ocular fundus blood flow imaging device according to claim 1, further comprising:
   means for adjusting a gap between the respective rectangular spots of the two laser beams.

9. The wide viewing angle ocular fundus blood flow imaging device according to claim 1, further comprising:
   means for projecting, when the ocular fundus is irradiated with the expanded laser beam, an incoherent light at a position in the ocular fundus at which the expanded laser beam is irradiated to illuminate the position, the means for projecting configured to project the incoherent light simultaneous with the irradiation of the expanded laser beam; and
   means for monitoring movement of an ocular fundus blood vessel image by means of a second observation system, the second observation system imaging the position on which the expanded laser beam is irradiated and the incoherent light is projected.

10. The wide viewing angle ocular fundus blood flow imaging device according to claim 9, wherein the means for monitoring collates ocular fundus image data obtained by the laser beam and ocular fundus image data obtained by the incoherent light.

11. A wide viewing angle ocular fundus blood flow imaging device comprising:
   means for irradiating an ocular fundus with an expanded laser beam;
   means for imaging light reflected from the ocular fundus on a 2-dimensional image sensor as a laser speckle; and
   means for measuring, for each pixel of the laser speckle, a change over time of the laser speckle generated on an image plane, and for displaying a blood flow map based on the measured change,
   wherein the means for irradiating comprises a projection system that employs two laser beams and turns each of the two laser beams into respective rectangular spots on the ocular fundus, wherein each of the respective rectangular spots is disposed on a different region of the ocular fundus, and the means for imaging comprises an observation system that images the rectangular spots on the 2-dimensional image sensor placed on the corresponding image plane, wherein as an internal fixation target for a subject whose eye is to be tested a fixation target is lit in a cross shape utilizing a light-emitting diode matrix.

12. A wide viewing angle ocular fundus blood flow imaging device comprising:
   means for irradiating an ocular fundus with an expanded laser beam;
   means for imaging light reflected from the ocular fundus on a 2-dimensional image sensor as a laser speckle; and
   means for measuring, for each pixel of the laser speckle, a change over time of the laser speckle generated on an image plane, and for displaying a blood flow map based on the measured change,
   wherein the means for irradiating comprises a projection system that employs two laser beams and turns each of the two laser beams into respective rectangular spots on the ocular fundus, wherein each of the respective rectangular spots is disposed on a different region of the ocular fundus, and the means for imaging comprises an observation system that images the rectangular spots on the 2-dimensional image sensor placed on the corresponding image plane, wherein the device has incorporated thereinto a mechanism for automatically driving the entire observation system in vertical and lateral directions in response to vertical and lateral movement of the fixation target.

13. A wide viewing angle ocular fundus blood flow imaging device comprising:
   means for irradiating an ocular fundus with an expanded laser beam;
   means for imaging light reflected from the ocular fundus on a 2-dimensional image sensor as a laser speckle; and
   means for measuring, for each pixel of the laser speckle, a change over time of the laser speckle generated on an image plane, and for displaying a blood flow map based on the measured change,
   wherein the means for irradiating comprises a projection system that employs two laser beams and turns each of the two laser beams into respective rectangular spots on the ocular fundus, wherein each of the respective rectangular spots is disposed on a different region of the ocular fundus, and the means for imaging comprises an observation system that images the rectangular spots on the 2-dimensional image sensor placed on the corresponding image plane, wherein the device has incorporated thereinto a mechanism for forming one large map by calculating relative positions between a plurality of maps and combining the maps based on light-emitting diode matrix coordinates of the fixation target.

14. A wide viewing angle ocular fundus blood flow imaging device comprising:
   means for irradiating an ocular fundus with an expanded laser beam;
   means for imaging light reflected from the ocular fundus on a 2-dimensional image sensor as a laser speckle; and
   means for measuring, for each pixel of the laser speckle, a change over time of the laser speckle generated on an image plane, and for displaying a blood flow map based on the measured change,
   wherein the means for irradiating comprises a projection system that employs two laser beams and turns each of the two laser beams into respective rectangular spots on the ocular fundus, wherein each of the respective rectangular spots is disposed on a different region of the ocular fundus, and the means for imaging comprises an observation system that images the rectangular spots on the 2-dimensional image sensor placed on the corresponding image plane, wherein the device has incorporated thereinto a mechanism that, when storing a measured blood flow map in a file, stores data for the positional coordinates of the fixation target when the eye is tested in a header part of the file or another database, reads these data when testing the eye the next time, and automatically sets the position of the fixation target.

15. The wide viewing angle ocular fundus blood flow imaging device according to claim 1, further comprising:
means for calculating a difference between data obtained on different eye testing occasions and displaying an image of increases and decreases in blood flow based on the calculated difference.

16. A wide viewing angle ocular fundus blood flow imaging device comprising:
means for irradiating an ocular fundus with an expanded laser beam;
means for imaging light reflected from the ocular fundus on a 2-dimensional image sensor as a laser speckle; and
means for measuring, for each pixel of the laser speckle, a change over time of the laser speckle generated on an image plane, and for displaying a blood flow map based on the measured change,
wherein the means for irradiating comprises a projection system that employs two laser beams and turns each of the two laser beams into respective rectangular spots on the ocular fundus, wherein each of the respective rectangular spots is disposed on a different region of the ocular fundus, and the means for imaging comprises an observation system that images the rectangular spots on the 2-dimensional image sensor placed on the corresponding image plane, wherein the device has incorporated thereinto a function for calculating an autocorrelation function with respect to a waveform of average blood flow in the ocular fundus and separating a series of map data arranged in chronological order using an average period by taking the time from the center of one peak to the next as one period, and a calculation function for determining the time relationship for optimum overlap by superimposing average blood flow waveforms of the group of separated maps.

17. A wide viewing angle ocular fundus blood flow imaging device comprising:
means for irradiating an ocular fundus with an expanded laser beam;
means for imaging light reflected from the ocular fundus on a 2-dimensional image sensor as a laser speckle; and
means for measuring, for each pixel of the laser speckle, a change over time of the laser speckle generated on an image plane, and for displaying a blood flow map based on the measured change,
wherein the means for irradiating comprises a projection system that employs two laser beams and turns each of the two laser beams into respective rectangular spots on the ocular fundus, wherein each of the respective rectangular spots is disposed on a different region of the ocular fundus, and the means for imaging comprises an observation system that images the rectangular spots on the 2-dimensional image sensor placed on the corresponding image plane, wherein the device has incorporated thereinto a function for retrieving as a signal an exposure timing of the above-mentioned 2-dimensional image sensor, irradiating the ocular fundus with laser only for the time for which each element of the sensor is exposed, and reducing the laser output for the time other than the above, thus reducing the amount of laser bombardment that the ocular fundus receives.

18. A wide viewing angle ocular fundus blood flow imaging device comprising:
means for irradiating an ocular fundus with an expanded laser beam;
means for imaging light reflected from the ocular fundus on a 2-dimensional image sensor as a laser speckle; and
means for measuring, for each pixel of the laser speckle, a change over time of the laser speckle generated on an image plane, and for displaying a blood flow map based on the measured change,
wherein the means for irradiating comprises a projection system that employs two laser beams and turns each of the two laser beams into respective rectangular spots on the ocular fundus, wherein each of the respective rectangular spots is disposed on a different region of the ocular fundus, and the means for imaging comprises an observation system that images the rectangular spots on the 2-dimensional image sensor placed on the corresponding image plane, wherein an emergent laser optical system is inserted between the subject's eye and an objective lens for observation of the ocular fundus so as to prevent intrusion of a specular reflection component of the laser spot into the blood flow image.

19. The wide viewing angle ocular fundus blood flow imaging device according to claim 1, further comprising:
means for changing a fixation target position during measurement of the blood flow, so that the influence of seams between a plurality of laser spots is prevented from appearing on the blood flow map.

20. A wide viewing angle ocular fundus blood flow imaging device comprising means for irradiating the ocular fundus with an expanded laser beam, means for imaging light reflected from the ocular fundus on a 2-dimensional image sensor as a laser speckle, and means for measuring for each pixel a change over time of the laser speckle generated on the image plane to thus display an image as a blood flow map, wherein the device comprises a blood flow measurement optical system that comprises a projection system that employs one laser beam and turns the beam into a rectangular spot on the ocular fundus, and an observation system that images the rectangular spot on an image sensor placed on the corresponding image plane and, furthermore, an emergent laser optical system is inserted between a subject's eye and an objective lens for observation of the ocular fundus so as to prevent intrusion of a specular reflection component of the laser spot into the blood flow image.

21. A wide viewing angle ocular fundus blood flow imaging device comprising means for irradiating the ocular fundus with an expanded laser beam, means for imaging light reflected from the ocular fundus on a 2-dimensional image sensor as a laser speckle, and means for measuring for each pixel a change over time of the laser speckle generated on the image plane to thus display an image as a blood flow map, wherein the device comprises a blood flow measurement optical system that comprises a projection system that employs one laser beam and turns the beam into a rectangular spot on the ocular fundus, and an observation system that images the rectangular spot on an image sensor placed on the corresponding image plane and, furthermore, the device has incorporated thereinto a mechanism for monitoring the movement of an ocular fundus blood vessel image by means of a different observation system from that for imaging such that, when the ocular fundus is irradiated with a laser beam so as to image the ocular fundus blood flow, the same position in the ocular fundus is simultaneously illuminated with incoherent light.

22. The wide viewing angle ocular fundus blood flow imaging device according to claim 21, wherein the monitoring mechanism comprises a method in which the ocular fundus image data obtained by laser and the ocular fundus image data obtained by incoherent light are collated.

23. A wide viewing angle ocular fundus blood flow imaging device comprising:
   means for irradiating an ocular fundus with an expanded laser beam;
   means for imaging light reflected from the ocular fundus on a 2-dimensional image sensor as a laser speckle;
   means for measuring for each pixel a change over time of the laser speckle generated on an image plane, and for displaying a blood flow map based on the measured change;
   a blood flow measurement optical system that comprises a projection system that employs one laser beam and turns the laser beam into a rectangular spot on the ocular fundus, and an observation system that images the rectangular spot on the 2-dimensional image sensor placed on the corresponding image plane;
   an optical system for observing a position of a laser beam spot passing through a pupil, and for obtaining image information based on the observed position; and
   means for carrying out appropriate control of positioning of the blood flow measurement optical system based on the obtained image information, wherein the means for carrying out appropriate control automatically drives the observation system of the blood flow measurement optical system in vertical and lateral directions in response to vertical and lateral movement of a fixation target.

24. A wide viewing angle ocular fundus blood flow imaging device comprising:
   a projector which projects at least two laser beams as at least two respective rectangular spots on an ocular fundus, wherein each of the at least two respective rectangular spots is disposed on a different region of the ocular fundus; and
   a capturing unit which captures, in response to the projected at least two laser beams on the ocular fundus, light reflected from the ocular fundus as a laser speckle; and
   a controller which measures, for each pixel of the laser speckle, a change over time of the laser speckle; and
   a display which displays a blood flow map based on the measured change.

* * * * *